(12) United States Patent
Li et al.

(10) Patent No.: US 7,029,902 B2
(45) Date of Patent: Apr. 18, 2006

(54) ISOLATED MONKEY CATHEPSIN S PROTEINS, NUCLEIC ACID MOLECULES ENCODING MONKEY CATHEPSIN S PROTEINS, AND USES THEREOF

(75) Inventors: Shyr-Jiann Li, San Francisco, CA (US); James Clark, San Mateo, CA (US); Hong Zhang, San Francisco, CA (US)

(73) Assignee: Applera Corporation, Norwalk, CT (US)

( * ) Notice: Subject to any disclaimer, the term of this patent is extended or adjusted under 35 U.S.C. 154(b) by 116 days.

(21) Appl. No.: 10/809,816

(22) Filed: Mar. 26, 2004

(65) Prior Publication Data

US 2005/0214774 A1 Sep. 29, 2005

(51) Int. Cl.
  *C12N 9/64* (2006.01)
  *C12N 15/57* (2006.01)
  *C12N 15/79* (2006.01)

(52) U.S. Cl. .................. 435/226; 435/69.1; 435/252.3; 435/320.1; 536/23.2

(58) Field of Classification Search ..................... None
  See application file for complete search history.

(56) References Cited

U.S. PATENT DOCUMENTS 5,501,969 A * 3/1996 Hastings et al. ....... 435/252.33
5,736,357 A * 4/1998 Bromme et al. ........... 435/69.1

(Continued)

OTHER PUBLICATIONS

Morton,P.A., Zachies,M.L., Giacoletto, K.S., Manning, J.A., Schwartz,B.D.,(1995) J. Immunol. 154, 137-150.
Hsieh, C.S., deRoos, P., Honey, K., Beers, C., and Rudensky, A.Y. (2002) *J. Immunol.* 168, 2618-2625.

(Continued)

*Primary Examiner*—Nashaat T. Nashed
*Assistant Examiner*—William W. Moore
(74) *Attorney, Agent, or Firm*—Celera Genomics; Justin D. Karjala

(57) ABSTRACT

The present invention provides isolated monkey Cathepsin S proteins and isolated nucleic acid molecules such as cDNA molecules that encode these monkey Cathepsin S proteins. The present invention specifically provides, for example, isolated monkey Cathepsin S proteins and encoding nucleic acid molecules, methods of producing the monkey Cathepsin S proteins, methods of identifying and screening modulators of the monkey Cathepsin S proteins, and methods of using these modulators to treat a human disease or disorders associated with an orthologous human Cathepsin S protein.

12 Claims, 4 Drawing Sheets

U.S. PATENT DOCUMENTS

| | | | | |
|---|---|---|---|---|
| 6,274,336 B1* | 8/2001 | Abdel-Meguid et al. | ...... | 435/23 |
| 6,383,793 B1* | 5/2002 | Hastings et al. | ............ | 435/226 |
| 6,387,629 B1* | 5/2002 | Schneider et al. | ............. | 435/6 |
| 6,387,682 B1* | 5/2002 | Hastings et al. | ............ | 435/226 |
| 6,423,507 B1* | 7/2002 | Hastings et al. | .............. | 435/23 |
| 6,475,487 B1* | 11/2002 | Hastings et al. | ......... | 424/130.1 |
| 6,475,766 B1* | 11/2002 | Hastings et al. | ............ | 435/226 |
| 6,544,767 B1* | 4/2003 | Bromme et al. | ............ | 435/226 |
| 6,680,375 B1* | 1/2004 | Hastings et al. | ......... | 530/389.1 |
| 6,800,473 B1* | 10/2004 | Santamaria et al. | ........ | 435/226 |
| 2003/0143714 A1* | 7/2003 | Lamers et al. | .............. | 435/226 |

OTHER PUBLICATIONS

Riese,R.J.,Mitchell,R.N., Villadangos,J.A.,Shi,G.P., Palmer, J.T., Karp, E.R., De Sanctis, G.T., Ploegh,H.L., and Chapman, H.A. (1998) *J. Clin. Invest.* 101, 2351-2363.

Nakagawa,T.Y., Brissette, E.H., Lira, P.D., Griffiths, R.J., Petrushova, N., Stock, J., McNeish, J.D., Eastman, S.E., Howard, E.D., Clarke, S.R., Rosloniec, E.F., Elliott, E.A., and Rudensky, A.Y. (1999) *Immunity* 10, 207-217.

Shi,G.-P., Villadangos, J.A., Dranoff, G.,Small, C., Gu, L., Haley,K.J., Rises, R., Ploegh, H.L., Chapman, H.A. (1999) *Immunity* 10, 197-206.

\* cited by examiner

Figure 1: cDNA sequence (and encoded amino acid sequence) of Cynomologous monkey Cathepsin S

```
   1   AGTTGAACTGAAATCTCCCTGCTGCTGCTTTGAAATCTTAGAAGAGAGCCCATCAATTCA
  61   AGGATTCTTACTGTAGGAGCACCTGCTGGTTCTATCACAATGAAACAGCTGGTTTGTGTG
                                         M  K  Q  L  V  C  V
                                         ♦
 121   CTCTTGGTGTGCTCCTCTGCAGTGGCGCAGTTGCATAAAGATCCTACCCTGGATCATCAC
       L  L  V  C  S  S  A  V  A  Q  L  H  K  D  P  T  L  D  H  H
 181   TGGCATCTCTGGAAGAAAACCTATGGCAAACAATACAAGGAAAAGAATGAAGAAGCAGTA
       W  H  L  W  K  K  T  Y  G  K  Q  Y  K  E  K  N  E  E  A  V
 241   CGACGTCTCATCTGGGAAAAGAATCTAAAGTTTGTGATGCTTCATAACCTGGAGCATTCA
       R  R  L  I  W  E  K  N  L  K  F  V  M  L  H  N  L  E  H  S
 301   ATGGGAATGCACTCATATGATCTGGGCATGAACCACCTGGGAGACATGACCAGTGAAGAA
       M  G  M  H  S  Y  D  L  G  M  N  H  L  G  D  M  T  S  E  E
 361   GTGATGTCTTTGATGAGTTCCCTGAGAGTTCCCAGCCAGTGGCAGAGAAATATCACATAT
       V  M  S  L  M  S  S  L  R  V  P  S  Q  W  Q  R  N  I  T  Y
                             ↓
 421   AAGTCAAACGCTAATCAGATATTGCCGGATTCTGTGGACTGGAGAGAGAAAGGGTGTGTT
       K  S  N  A  N  Q  I  L  P  D  S  V  D  W  R  E  K  G  C  V
 481   ACTGAAGTGAAATATCAAGGTTCTTGTGGTGCTTGCTGGGCTTTCAGTGCTGTGGGGGCC
       T  E  V  K  Y  Q  G  S  C  G  A  C  W  A  F  S  A  V  G  A
 541   CTGGAAGCACAGCTGAAGCTGAAAACAGGAAAGCTGGTGTCTCTCAGTGCCCAGAACCTG
       L  E  A  Q  L  K  L  K  T  G  K  L  V  S  L  S  A  Q  N  L
 601   GTGGATTGCTCAACTGAAAAATATGGAAACAAAGGCTGCAATGGTGGCTTCATGACAAGG
       V  D  C  S  T  E  K  Y  G  N  K  G  C  N  G  G  F  M  T  R
 661   GCTTTCCAGTACATCATTGATAACAACGGCATCGACTCAGACGCTTCCTATCCCTACAAA
       A  F  Q  Y  I  I  D  N  N  G  I  D  S  D  A  S  Y  P  Y  K
 721   GCCACGGATCAGAAGTGTCAATATGACTCAAAATATCGTGCTGCCACATGTTCAAAGTAT
       A  T  D  Q  K  C  Q  Y  D  S  K  Y  R  A  A  T  C  S  K  Y
 781   ACTGAACTTCCTTATGGCAGAGAAGATGTCCTGAAAGAAGTTGTGGCCAATAAAGGCCCA
       T  E  L  P  Y  G  R  E  D  V  L  K  E  V  V  A  N  K  G  P
 841   GTGTCTGTTGGTGTGGATGCGAGTCATCCTTCTTTCTTCCTCTACAGAAGTGGTGTCTAC
       V  S  V  G  V  D  A  S  H  P  S  F  F  L  Y  R  S  G  V  Y
 901   TATGAACCATCCTGTACTCAGAATGTGAATCATGGTGTACTTGTGGTTGGCTATGGTGTT
       Y  E  P  S  C  T  Q  N  V  N  H  G  V  L  V  V  G  Y  G  V
 961   CTTAACGGGAAAGAATACTGGCTTGTGAAAAACAGCTGGGGCCGCAACTTTGGTGAAGAA
       L  N  G  K  E  Y  W  L  V  K  N  S  W  G  R  N  F  G  E  E
1021   GGATATATTCGGATGGCAAGAAATAAAGGAAATCATTGTGGGATTGCTAGTTTCCCCTCT
       G  Y  I  R  M  A  R  N  K  G  N  H  C  G  I  A  S  F  P  S
1081   TACCCAGAAATCTAGAGAGGATCTCTTCTTTTTATAACAAATCAAGAAAATATGAAGCAC
       Y  P  E  I  *                                                    SEQ ID NO:2
1141   TTTCTCTTAACTTAATTTTTCCTGCTGTATCCAGAAGAAATAATTGTGTCACGATTAATG
1201   TGTATTTACTGTACTAATTAAAAAATATAGTTTGAGGCCGGGCACGGTGGCTCACGCCTG
1261   TAATCCCAGTACTTTGGGAGGCCAAGGCAGGCATATCAACTTGAGGCCAGGAGTTAAAGA
1321   CAGGCCTGGCTAACATGGTGAAACCCCGTCTCTACTAAAAATACAAAACATTAGCGGAGC
1381   GTAATGGTGCATGCCTGTAATCCCAGCTACTTGGGAGGCTGAAGCACAAGATTCCTTGAA
1441   CCCAAGAGGTTGAGGCTGTGGTGAGCTGAGACCACACCACTGTACTCCAGCCTGGACAAC
1501   AGAGTGGAGACTCTGTTTCAAAAAAACAGAAAAGATAATATAGTTTGATTCTTCGTTTTT
1561   TAAAATTTGCAAACCTCAGGAAAAAGTTTGCTAAGTAAATTAGTAGTGTACTATAGATAT
1621   AACTGTATAAAAATTGTTCAACCTAAAACAATCTGTCATTGTTCATTGTTTTATTTTATA
1681   CTCTTTGTCTTTTTAAGACCCCTGATAGCCTTTTGTAACTTGATGGCTTAAAAGTACTTA
1741   ATAAATCTGCCATTTCAAATTTCATTTCAAAAAAAAAAAAAAAAAAAAAAAAAAAAAAA      SEQ ID NO:1
```

♦ = cleavage site for pre-sequence

↓ = cleavage site for pro-sequence

* = stop codon

FIGURE 1

Figure 2: Alignment of cathepsin S amino acid sequences from Cynomologous monkey (SEQ ID NO:2, as shown in Fig. 1), human (Genbank accession number BC002642.2), monkey sml cells (*Saimiri boliviensis*), dog (*Canis familiaris*; Genbank accession number AY156692), and mouse (*Mus musculus*; Genbank gi3850787), followed by a consensus sequence.

"cyno cats preprotein" = Cynomologous monkey = SEQ ID NO:2
"smlmonkey cats" = monkey sml cells (*Saimiri boliviensis*) = SEQ ID NO:3
"hcats prepropro.txt" = human (*Homo sapiens*) = SEQ ID NO:4
"dog cats" = dog (*Canis familiaris*) = SEQ ID NO:5
"mouse cats prepro" = mouse (*Mus musculus*) = SEQ ID NO:6
(consensus sequence = SEQ ID NO:7)

FIGURE 2A

ClustalW Formatted Alignments

```
                         10                  20                  30                  40
cyno cats preprotein   M K Q L V C V L L V C S S A V A Q L H K D P T L D H H W H L W K K T Y G K Q Y K
smlmonkey cats         M K Q L V C V L F V C S S A V T Q L H K D P T L D H H W N L W K K T Y G K Q Y K
hcats prepropro.txt    M K R L V C V L L V C S S A V A Q L H K D P T L D H H W H L W K K T Y G K Q Y K
dog cats               M K W L V G L L P L C S Y A V A Q V H K D P T L D H H W N L W K K T Y S K Q Y K
mouse catsprepro       M A V L D A P G V L C G N G A T A E R - - P T L D H H W D L W K K T H E K E Y K
                       M K . L V C V L . V C S S A V A Q L H K D P T L D H H W . L W K K T Y G K Q Y K 50                  60                  70                  80
cyno cats preprotein   E K N E E A V R R L I W E K N L K F V M L H N L E H S M G M H S Y D L G M N H L
smlmonkey cats         E K N E E A V R R L I W E K N L K F V M L H N L E H S M G M H S Y D L G M N H L
hcats prepropro.txt    E K N E E A V R R L I W E K N L K F V M L H N L E H S M G M H S Y D L G M N H L
dog cats               E E N E E V A R R L I W E K N L K F V M L H N L E H S M G M H S Y D L G M N H L
mouse catsprepro       D K N E E E V R R L I W E K N L K F I M I H N L E Y S M G M H T Y Q V G M N D M
                       E K N E E A V R R L I W E K N L K F V M L H N L E H S M G M H S Y D L G M N H L 90                 100                 110                 120
cyno cats preprotein   G D M T S E E V M S L M S S L R V P S Q W Q R N I T Y K S N A N Q L L P D S V D
smlmonkey cats         G D M T S E E V M S L M S S L R V P N Q W Q R N I T Y K S N P N Q M L P D S V D
hcats prepropro.txt    G D M T S E E V M S L M S S L R V P S Q W Q R N I T Y K S N P N W I L P D S V D
dog cats               G D M T G E E V I S L M G S L R V P S Q W Q R N V T Y R S N S N Q K L P D S V D
mouse catsprepro       G D M T N E E I L C R M G A L R I P R Q S P K T V T F R S Y S N R T L P D T V D
                       G D M T S E E V M S L M S S L R V P S Q W Q R N I T Y K S N . N Q . L P D S V D 130                 140                 150                 160
cyno cats preprotein   W R E K G C V T E V K Y Q G S C G A C W A F S A V G A L E A Q L K L K T G K L V
smlmonkey cats         W R E K G C V T E V K Y Q G S C G A C W A F S A V G A L E A Q L K L K T G K L V
hcats prepropro.txt    W R E K G C V T E V K Y Q G S C G A C W A F S A V G A L E A Q L K L K T G K L V
dog cats               W R E K G C V T E V K Y Q G S C G A C W A F S A V G A L E A Q L K L K T G K L V
mouse catsprepro       W R E K G C V T E V K Y Q G S C G A C W A F S A V G A L E G Q L K L K T G K L I
                       W R E K G C V T E V K Y Q G S C G A C W A F S A V G A L E A Q L K L K T G K L V 170                 180                 190                 200
cyno cats preprotein   S L S A Q N L V D C S T - E K Y G N K G C N G G F M T R A F Q Y I I D N N G I D
smlmonkey cats         S L S A Q N L V D C S - - E K Y G N K G C N G G F M T E A F Q Y I I D N K G I D
hcats prepropro.txt    S L S A Q N L V D C S T - E K Y G N K G C N G G F M T T A F Q Y I I D N K G I D
dog cats               S L S A Q N L V D C S T - E K Y G N K G C N G G F M T T A F Q Y I I D N N G I D
mouse catsprepro       S L S A Q N L V D C S N E E K Y G N K G C G G G Y M T E A F Q Y I I D N G G I E
                       S L S A Q N L V D C S T   E K Y G N K G C N G G F M T . A F Q Y I I D N . G I D 210                 220                 230                 240
cyno cats preprotein   S D A S Y P Y K A T D Q K C Q Y D S K Y R A A T C S K Y T E L P Y G R E D V L K
smlmonkey cats         S E A S Y P Y K A T D Q K C Q Y D S K Y R A A T C S K Y T E L P Y G R E D V L K
hcats prepropro.txt    S D A S Y P Y K A M D Q K C Q Y D S K Y R A A T C S K Y T E L P Y G R E D V L K
dog cats               S E A S Y P Y K A M N G K C R Y D S K K R A A T C S K Y T E L P F G S E D A L K
mouse catsprepro       A D A S Y P Y K A M D E K C H Y N S K N R A A T C S R Y I Q L P F G D E D A L K
                       S D A S Y P Y K A M D Q K C Q Y D S K Y R A A T C S K Y T E L P Y G R E D V L K 250                 260                 270                 280
cyno cats preprotein   E V V A N K G P V S V G V D A S H P S F F L Y R S G V Y Y E P S C T Q N V N H G
smlmonkey cats         E A V A N K G P V C V G V D A S H P S F F L Y R S G V Y Y D P A C T Q K V N H G
hcats prepropro.txt    E A V A N K G P V S V G V D A R H P S F F L Y R S G V Y Y E P S C T Q N V N H G
dog cats               E A V A N K G P V S V A I D A S H Y S F F L Y R S G V Y Y E P S C T Q N V N H G
mouse catsprepro       E A V A T K G P V S V G I I D A S H S S F F Y K S G V Y D D P S C T G N V N H G
                       E A V A N K G P V S V G V D A S H P S F F L Y R S G V Y Y E P S C T Q N V N H G 290                 300                 310                 320
cyno cats preprotein   V L V V G Y G V L N G K E Y W L V K N S W G R N F G E E G Y I R M A R N K G N H
smlmonkey cats         V L V I G Y G D L N G K E Y W L V K N S W G S N F G E Q G Y I R M A R N K G N H
hcats prepropro.txt    V L V V G Y G D L N G K E Y W L V K N S W G H N F G E E G Y I R M A R N K G N H
dog cats               V L V V G Y G N L N G K D Y W L V K N S W G L N F G D Q G Y I R M A R N S G N H
mouse catsprepro       V L V V G Y G T L D G K D Y W L V K N S W G L N F G D Q G Y I R M A R N N K N H
                       V L V V G Y G . L N G K E Y W L V K N S W G . N F G E Q G Y I R M A R N K G N H 330                 340                 350                 360
cyno cats preprotein   C G I A S F P S Y P E I
smlmonkey cats         C G I A S Y P S Y P E I
hcats prepropro.txt    C G I A S F P S Y P E I
dog cats               C G I A S Y P S Y P E I
mouse catsprepro       C G I A S Y C S Y P E I
                       C G I A S Y P S Y P E I
```

FIGURE 2B

Figure 3: Purification of monkey Cathepsin S (Gelcode stained gel)

ISOLATED MONKEY CATHEPSIN S PROTEINS, NUCLEIC ACID MOLECULES ENCODING MONKEY CATHEPSIN S PROTEINS, AND USES THEREOF

FIELD OF THE INVENTION

The present invention is in the field of cathepsin S proteins, recombinant DNA molecules, and protein production. The present invention specifically provides isolated cathepsin S proteins of Cynomologous monkeys, and isolated nucleic acid molecules encoding such monkey cathepsin S proteins, all of which are useful in the development of human therapeutics and diagnostic compositions and methods.

BACKGROUND OF THE INVENTION

Proteases

In general, proteases typically affect protein cleavage, processing, and/or turnover. Proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre- or pro-protein precursors that are processed by proteolytic degradation to produce an active moiety. Thus, complex and highly regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner AP Press, NY 1998). Also, for a review of the various uses of proteases as drug targets, see: Weber M, Emerging treatments for hypertension: potential role for vasopeptidase inhibition; Am J Hypertens 1999 November;12(11 Pt 2):139S–147S; Kentsch M, Otter W, Novel neurohormonal modulators in cardiovascular disorders. The therapeutic potential of endopeptidase inhibitors, Drugs R D 1999 April;1(4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann N Y Acad Sci 1999 Jun. 30;878:61–72; McKerrow J H, Engel J C, Caffrey C R, Cysteine protease inhibitors as chemotherapy for parasitic infections, Bioorg Med Chem 1999 April;7(4):639–44; Rice K D, Tanaka R D, Katz B A, Numerof R P, Moore W R, Inhibitors of tryptase for the treatment of mast cell-mediated diseases, Curr Pharm Des 1998 October;4(5):381–96; Materson B J, Will angiotensin converting enzyme genotype, receptor mutation identification, and other miracles of molecular biology permit reduction of NNT Am J Hypertens 1998 August;11(8 Pt 2):138S–142S.

Cathepsin S

Cathepsin S is a lysosomal cysteine protease that catalyzes the removal of the invariant chain (Ii) from MHC class II molecules (Morton, P. A., Zacheis, M. L., Giacoletto, K. S., Manning, J. A., Schwartz, B. D., (1995) *J. Immunol.* 154, 137–150). Ii serves dual functions. Ii serves as a molecular chaperon that promotes the MHC class II/Ii complex exit from the ER to the endosomal system through the secretory pathway. Ii also functions as a molecular inhibitor that occupies the peptide-binding pocket of MHC class II to prevent premature binding of native peptides in the secretory pathway (Hsieh, C. S., deRoos, P., Honey, K., Beers, C., and Rudensky, A. Y. (2002) *J. Immunol.* 168, 2618–2625). Experiments using protease inhibitors and knockout mice have clearly shown that cathepsin S is involved in proteolytic clearance of Ii from MHC class II molecules (Riese, R. J., Mitchell, R. N., Villadangos, J. A., Shi, G. P., Palmer, J. T., Karp, E. R., De Sanctis, G. T., Ploegh, H. L., and Chapman, H. A. (1998) *J. Clin. Invest.* 101, 2351–2363; Nakagawa, T. Y., Brissette, E. H., Lira, P. D., Griffiths, R. J., Petrushova, N., Stock, J., McNeish, J. D., Eastman, S. E., Howard, E. D., Clarke, S. R., Rosloniec, E. F., Elliott, E. A., and Rudensky, A. Y. (1999) *Immunity* 10, 207–217). Inhibition of cathepsin S precludes antigen loading to MHC class II molecules and disables the antigen-presenting cell, thereby preventing the antigen-presenting cell from presenting antigen to CD4+ T cells (Shi, G.-P., Villadangos, J. A., Dranoff, G., Small, C., Gu, L., Haley, K. J., Rises, R., Ploegh, H. L., Chapman, H. A. (1999) *Immunity* 10, 197–206). Selective inhibition of cathepsin S is therefore considered to be therapeutically useful to attenuate the elevated immune responses found in many autoimmune disorders.

To investigate the effectiveness of cathepsin S inhibitors, it is typically necessary to evaluate species-specific cathepsin S activity in different animal autoimmune disease models. In particular, to develop cathepsin S inhibitors for the treatment of human disorders, it is typically desirable to test candidate inhibitor compounds against cathepsin S proteins of non-human primates, such as monkeys. Non-human primates, because they are more closely related to humans than rodents and other laboratory animals, can more accurately predict the effectiveness (as well as toxicity and other undesirable side effects) of the inhibitor compound in humans, and are therefore advantageous for use as animal models for evaluating the use of potential therapeutic compounds for treating human disease, prior to administration of the compounds to humans.

Consequently, because cathepsin S proteins are well established in the art as playing key roles in important human diseases (such as autoimmune disorders), and because monkeys serve as an optimal animal model for evaluating candidate therapeutic compounds for the treatment of human diseases, a need exists in the art for isolated cathepsin S proteins, and encoding nucleic acid molecules, from non-human primates such as monkeys.

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field, see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N. Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

Mammalian Models of Human Disease

Non-human primates such as monkeys, as well as rodents such as mice (*Mus musculus*) and other animals such as rabbits and guinea pigs, are commonly used in biomedical research as model systems for studying human diseases and for developing therapeutic and diagnostic agents for human diseases. Detailed descriptions of techniques and protocols for manipulating and using such animal models of human disease, particularly mouse models, such as techniques for using homologous recombination to produce mutant mouse strains and mutant cell lines with specific genes inactivated (e.g., "knockout" mice), are readily available, and the techniques described for mice can be applied to monkeys and other non-human primates as well as other laboratory animals. For example, for a review of mouse models for studying gene/protein functions and interactions, cell biology, and human diseases, including mouse mutagenesis techniques currently used in the art, see *Current Protocols in Molecular Biology*, John Wiley & Sons, Inc., "Manipulating the Mouse Genome", chapter 23, supplements 51–53 (2000–2001); Nolan et al., *Nat Genet* 2000 August;25(4): 440–3; Brown, *J Inherit Metab Dis* 1998 August;21(5): 532–9; Nolan, *Pharmacogenomics* 2000 August; 1(3):243–55; Justice, *Nat Rev Genet* 2000 November; 1(2): 109–15; and Mansuy et al., *Exp Physiol* 2000 November; 85(6):661–79.

Protease proteins, particularly cathepsin S proteases, are a major target for drug action and development, and the monkey provides an optimal animal model in which to study these protease proteins and the diseases with which they are associated. Accordingly, it is valuable to the field of pharmaceutical development to identify and characterize previously unknown members of this subfamily of protease proteins in the monkey. The present invention advances the state of the art by providing isolated monkey cathepsin S proteins and encoding nucleic acid molecules.

SUMMARY OF THE INVENTION

The present invention is based in part on the cloning, expression, and isolation of monkey cathepsin S polypeptides and encoding nucleic acid molecules such as cDNA molecules. These unique monkey polypeptides, and nucleic acid molecules that encode these polypeptides, are useful, for example, in the development, screening, and evaluation of human therapeutic agents (e.g., small molecule compounds, antibodies, therapeutic proteins, nucleic acid agents such as RNAi or antisense agents, etc.), particularly therapeutic agents that target cathepsin S, such as cathepsin S inhibitors.

BRIEF DESCRIPTION OF THE FIGURES

FIG. 1 provides the nucleotide sequence of a cDNA molecule (SEQ ID NO:1) that encodes a Cynomologous monkey cathepsin S polypeptide (SEQ ID NO:2).

FIGS. 2A–2B (collectively referred to herein as FIG. 2) provide an alignment of cathepsin S amino acid sequences from Cynomologous monkey (SEQ ID NO:2), monkey sml cells (*Saimiri boliviensis*) (SEQ ID NO:3), human (Genbank accession number BC002642.2) (SEQ ID NO:4), dog (*canis familiaris;* Genbank accession number AY156692) (SEQ ID NO:5), and mouse (*Mus musculus;* Genbank gi3850787) (SEQ ID NO:6). A consensus sequence (SEQ ID NO:7) is also shown below these five sequences.

DETAILED DESCRIPTION OF THE INVENTION

General Description

Figure 3:
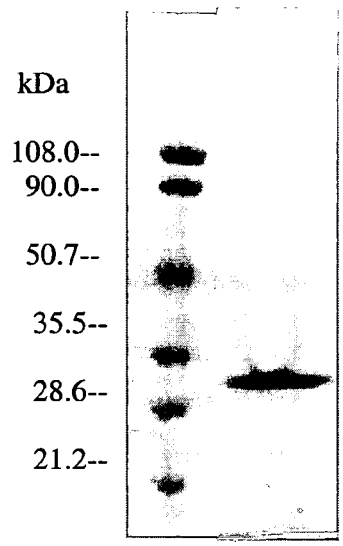
FIG. 3 provides an image of a Gelcode stained gel showing purification of monkey cathepsin S.

The present invention is based on the cloning, expression, and purification/isolation of cathepsin S proteins (cathepsin S may be interchangeable referred to as CatS) from Cynomologous monkeys. Cathepsin S is a lysosomal cysteine protease. The present invention provides amino acid sequences of Cynomologous monkey cathepsin S proteins, and nucleic acid molecules such as cDNA sequences that encode these monkey cathepsin S proteins. The present invention also provides methods of expressing/producing and isolating the monkey cathepsin S proteins, methods of identifying modulators of the monkey cathepsin S proteins (such as by using the monkey cathepsin S protein in screening assays to screen candidate compounds that target the cathepsin S protein, such as cathepsin S inhibitors), and methods of using these modulators to treat human disease or disorders associated with an orthologous human cathepsin S protein.

The 1.7 kb full-length Cynomologous cathepsin S cDNA, which is shown in FIG. 1 as SEQ ID NO:1, shares 96.3% overall nucleotide sequence identity with the human cathepsin S cDNA. The complete Cynomologous monkey pre-pro-CatS protein is a 331 amino acid protein with 96.7% identity to that of human (an alignment comparing cathepsin S amino acid sequences from multiple different species is shown in FIG. 2). There are ten amino acid sequence substitutions compared to the human protein sequence (see FIG. 2). Three of the ten amino acid substitutions are in the "pre-pro" region of the protein that is cleaved off and does not become part of the "mature" CatS. The other seven amino acid substitutions occur in the mature CatS sequence, and two of these seven substitutions are predicted to affect the enzyme structure and/or interactions between the enzyme and compounds such as CatS inhibitor compounds. Specifically, an Arg to Ser substitution exists at residue 256, which forms the S1' pocket, and a Thr to Arg substitution exists at residue 188, which is expected to affect the structure of the S2 and S3 pockets. The other eight amino acid substitutions are (listed in the format of: monkey amino acid/residue number/human amino acid): Q3R, A111P, Q113W, N197K, T210M, V242A, V288D, and R303H.

The monkey pro-CatS can be expressed and purified from yeast (see FIG. 3) and the enzyme is fully active after the pro-peptide is processed auto-catalytically in vitro. The availability of significant quantities of active CatS will facilitate the understanding of CatS interactions with different inhibitor compounds and will facilitate the evaluation of inhibitor compounds in a monkey disease model.

In FIG. 1, the diamond symbol at nucleotide 151 represents the cleavage site for the pre-sequence. Thus, the amino acid sequence of the pro-sequence begins with leucine ("L"), histidine ("H"), lysine ("K"). The down-arrow symbol at nucleotide 443 represents the cleavage site for the pro-sequence. Thus, the amino acid sequence of the mature enzyme begins with leucine ("L"), proline ("P"), aspartic acid ("D").

The peptides that are provided by the present invention are useful for the development of commercially important products and services, for example. The art has clearly established the commercial importance of cathepsin S proteins. Some of the more specific features of the peptides of the present invention, and the uses thereof, are described herein, particularly in the Background of the Invention and/or are known within the art for cathepsin S proteins.

As used herein, the terms "subject(s)", "individual(s)", and "patient(s)" may refer to monkeys or other non-human primates, humans, or any other animal. The methods and compositions provided by the present invention, particularly the monkey protease proteins and encoding nucleic acid molecules, are especially useful for studying human diseases and for developing drugs/therapeutic agents in a monkey (or other non-human primate) model in order to treat human diseases/disorders and to evaluate candidate therapeutic compounds. However, the present invention is not so limited and may also be useful for studying diseases/disorders in a monkey model that affect any animal and for developing therapeutic treatments for use in any animal. For example, the agents of the present invention may be used in a monkey model to develop veterinary pharmaceutical/therapeutic agents for treating diseases that affect domesticated animals and/or commercially valuable livestock such as cows and pigs. Additionally, it would be apparent to one of ordinary skill in the art that the compositions of the present invention may also be used in other animal model systems, particularly in those closely related to the Cynomologous monkey, such as other monkey species and other non-human primates.

Specific Embodiments

Peptide Molecules

The present invention provides nucleic acid molecules that encode monkey cathepsin S proteins (protein and cDNA sequences are provided in FIG. 1). The protein sequences provided in FIG. 1, as well as the obvious variants described herein, particularly allelic variants as identified herein and using the information in FIG. 1, will be referred to herein as the cathepsin S peptides/proteins, protease peptides/proteins, or peptides/proteins of the present invention. The terms "protein", "peptide", and "polypeptide" are used herein interchangeably.

The present invention provides isolated peptide and protein molecules that consist of, consist essentially of, or comprise the amino acid sequence of the cathepsin S protein disclosed in FIG. 1 (encoded by the cDNA sequence which is also shown in FIG. 1), as well as all obvious variants of these proteins that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequence provided in FIG. 1 (SEQ ID NO:2), for example, proteins encoded by the cDNA nucleic acid sequence shown in FIG. 1 (SEQ ID NO:1). The amino acid sequence of such a protein is provided in FIG. 1. A protein consists of an amino acid sequence when the amino acid sequence is the final amino acid sequence of the protein.

The present invention further provides proteins that consist essentially of the amino acid sequence provided in FIG. 1 (SEQ ID NO:2), for example, proteins encoded by the cDNA nucleic acid sequence shown in FIG. 1 (SEQ ID NO:1). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequence provided in FIG. 1 (SEQ ID NO:2), for example, proteins encoded by the cDNA nucleic acid sequence shown in FIG. 1 (SEQ ID NO:1). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be madelisolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but-is:not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PC R amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a OST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence; present in the paralog family and the evolutionary distance between the orthologs.

To determine the percent identity of two amino acid sequences or two nucleic acid sequences, the sequences are aligned for optimal-comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein.

Allelic variants of a protease peptide can readily be identified as being a monkey protein having a high degree (significant) of sequence homology/identity to at least a portion of the protease peptide as well as being encoded by the same genetic locus as the protease peptide provided herein. As used herein, two proteins (or a region of the proteins) have significant homology when the amino acid sequences are typically at least about 70–80%, 80–90%, and more typically at least about 90–95, 96, 97, 98, or 99% homologous. A significantly homologous amino acid sequence, according to the present invention, will be encoded by a nucleic acid sequence that will hybridize to a protease peptide encoding nucleic acid molecule under stringent conditions as more fully described below.

Paralogs of a protease peptide can readily be identified as having some degree of significant sequence homology/identity to at least a portion of the protease peptide, as being encoded by a monkey gene, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the monkey protease peptide as well as being encoded by a gene from another organism. Preferred orthologs will be isolated from mammals, preferably humans or other primates, for the development of human therapeutic targets and agents. Such orthologs will be encoded by a nucleic acid sequence that will hybridize to a monkey protease-encoding nucleic acid molecule under moderate to stringent conditions, as more fully described below, depending on the degree of relatedness of the two organisms yielding the proteins.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrates ability to participate in a signaling pathway, etc. Fully functional variants typically contain only conservative variation or variation in non-critical residues or in noncritical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), and can also be predicted based on the alignment of cathepsin S amino acid sequences from multiple species, as shown in FIG. 2 (since amino acid residues that are more conserved across species may typically be predicted to be more likely to have a functional affect). Alanine-scanning mutagenesis introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, proteases isolated from the monkey, and their human/mammalian orthologs, serve as targets for identifying agents for use in mammalian therapeutic applications, e.g. a human drug, particularly in modulating a biological or pathological response in a cell or tissue that expresses the protease. A large percentage of pharmaceutical agents are being developed that modulate the activity of protease proteins, particularly cathepsin S proteases (see Background of the Invention). The structural and functional information provided in the Background and Figures provide specific and substantial uses for the molecules of the present invention. Such uses can readily be determined using the information provided herein, that which is known in the art, and routine experimentation.

The proteins of the present invention (including variants and fragments that may have been disclosed prior to the present invention) are useful in biological assays to evaluate cathepsin S proteases and/or compounds that target cathepsin S proteases, such as cathepsin S inhibitors. Such assays typically involve any of the known protease functions or activities or properties useful for diagnosis and treatment of protease-related conditions, especially functions or activities or properties specific to cathepsin S proteases, particularly in cells and tissues that express the protease.

The proteins of the present invention are also useful in drug screening assays, in cell-based or cell-free systems. Cell-based systems can be native, i.e., cells that normally express the protease, as a biopsy or expanded in cell culture. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in a monkey or other animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary:skill in the art or that can be readily identified using the information provided herein. Specifically, a biological function of a cell or tissues that expresses the protease can be assayed.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate than that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then-combined with the cell lysates (e.g., $^{35}$S-labeled) and the candidate compound, and the mixture incubated under conditions conducive to complex fofoation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in a monkey or other animal model system. Such model systems are well known in the art and can readily be employed in this context.

Modulators of protease protein activity identified according to these drug-screening assays can be used to treat a subject with a disorder mediated by the protease pathway, by treating cells or tissues that express the protease. These methods of treatment include the steps of administering a modulator of protease activity in a pharmaceutical composition to a subject in need of such treatment, the modulator being identified as described herein. The subject is typically a human, but may be any other vertebrate or invertebrate animal that one desires to treat using a compound identified-according to the screening assays provided herein that utilize the monkey protease proteins/genes of the present invention. For example, the subject may be a commercially valuable or domesticated animal, such as a cow, pig, horse, etc.

In yet another aspect of the invention, the protease proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in a monkey or other appropriate animal model. For example, an agent identified as described herein (e.g., a protease-modulating agent, an antisense protease nucleic acid molecule, a protease-specific antibody, or a protease-binding partner) can be used in a monkey or other animal model to determine the efficacy, toxicity, or side effects of treatment with such an agent. Alternatively, an agent identified as described herein can be used in a monkey or other animal model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. The method typically involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected subjects. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Accordingly, methods for treatment can include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a mouse, rat, rabbit, or monkey. The full-length protein, an antigenic peptide fragment or a fusion protein can be used. Particularly important fragments are those covering functional domains, and domains of sequence homology or divergence amongst the family, such as those that can readily be identified using protein alignment methods and as presented in FIG. 2.

Antibodies are preferably prepared from regions or discrete fragments of the protease proteins. Antibodies can be prepared from any region of the peptide as described herein. However, preferred regions will include those involved in function/activity and/or protease/binding partner interaction.

Sequence alignment, such as that provided in FIG. 2, can be used to identify conserved and unique sequence fragments, and other particularly important protein regions.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness.

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 (SEQ ID NO:1), or any nucleic acid molecule that encodes the protein provided in FIG. 1 (SEQ ID NO:2). A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 (SEQ ID NO:1), or any nucleic acid molecule that encodes the protein provided in FIG. 1 (SEQ ID NO:2). A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 (SEQ ID NO:1), or any nucleic acid molecule that encodes the protein provided in FIG. 1 (SEQ ID NO:2). A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

Both coding and non-coding sequences may be encompassed by the present invention. For example, the nucleic acid molecules of the present invention may contain genomic intronic sequences, 5' and 3' non-coding sequences, gene regulatory regions and non-coding intergenic sequences. In general such sequence features can readily be identified using computational tools known in the art. As discussed below, some of the non-coding regions, particularly gene regulatory elements such as promoters, are useful for a variety of purposes, e.g., control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in the Figures. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in a genomic sequence.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95, 96, 97, 98, or 99% homologous to the nucleotide sequence (SEQ ID NO:1) shown in FIG. 1 or a fragment of this sequence. Such nucleic acid molecules can readily be identified as being able to hybridize under moderate to stringent conditions, to the nucleotide sequence shown in FIG. 1 or a fragment of the sequence. Allelic variants can readily be determined by genetic locus of the encoding gene.

As used herein, the term "hybridizes under stringent conditions" is intended to describe conditions for hybridization and washing-under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide shown in FIG. 1 (SEQ ID NO:2) and to isolate cDNA and genomic clones that correspond to variants (alleles, orthologs, etc.) producing the same or related peptides shown in FIG. 1.

The probe can correspond to any sequence along the entire length of the nucleic acid molecules shown in FIG. 1. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic monkeys or other non-human animals expressing all, or a part, of the nucleic acid molecules and peptides.

The nucleic acid molecules are also useful as hybridization probes for determining the presence, level, form and distribution of nucleic acid expression. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. An antisense nucleic acid molecule is generally designed to be complementary to a region of mRNA expressed by the gene so that the antisense molecule can hybridize to the mRNA and thereby block translation of mRNA into protein. Alternatively, an antisense nucleic acid molecule can hybridize to a region of the gene involved in transcription in order to block transcription. Antisense technology is well established in the art and extensively reviewed in *Antisense Drug Technology: Principles, Strategies, and Applications,* Crooke (ed.), Marcel Dekker, Inc.: New York (2001).

Thus, a class of antisense molecules can be used to inactivate mRNA in order to decrease expression of protease-encoding nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIG. 1 (SEQ ID NO:1).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the monkey genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the monkey genome disclosed herein or an orthologous fragment of the human genome; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. One of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila,* animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification., A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:3140 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kuijan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195,(1987)).

The expression vectors listed herein are provided by way of example only of the well-known vectors available to those of ordinary skill in the art that would be useful to express the nucleic acid molecules. One of ordinary skill in the art would be aware of other vectors suitable for maintenance propagation or expression of the nucleic acid molecules, described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to one of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a monkey or a rodent such as a mouse or rat, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a monkey or mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the protease protein to particular cells.

Methods for generating non-human transgenic animals via embryo manipulation and microinjection have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is, mutations that substantially or completely eliminate one or more protease protein functions.

Knockout Animal Models

The monkey Cathepsin S nucleic acid molecules disclosed herein are useful for generating "knockout" monkeys, as well as other non-human animals, in which specific genes are altered, such as to become inactivated or inhibited in function or expression. This alteration of specific genes is useful for, for example, elucidating specific disease-associated processes that the gene/encoded protein may be involved in, thereby revealing or validating potential therapeutic targets, or for defining the activity of a pharmaceutical compound.

Generally, an animal such as a monkey in which one or more genes or fragments thereof is intentionally altered, such as by deletion or disruption of the entire gene or a fragment thereof, is referred to as a "knockout" animal. Such alteration can be produced by, for example, homologous recombination or retrovirus integration. Generally, knockout animals are produced for the purpose of defining the phenotype of an animal lacking a particular gene segment (or in which the gene segment is present but disrupted, such as by insertion of an exogenous nucleic acid-fragment such as a retrovirus, transposon, transgene, a nucleic acid construct or cassette such as an insertion construct as described below, or a nucleic acid construct/cassette having a positive and/or negative selectable marker such as neomycin resistance, neo), in which the function and/or expression of one or more genes may be inactivated or inhibited. Producing alterations in genes to generate knockout animals may also be referred to as gene targeting. An animal in which one or more fragments of exogenous nucleic acid are introduced into the animal's genome, whether for the purposes of over-expressing one or more genes (e.g., by microinjection into the pronucleus of a fertilized monkey oocyte, as described above) or for the purpose of disrupting a gene to produce a knockout animal (e.g., by insertion of a transgene into a target gene in order to inactivate the target gene) may be interchangeably referred to as a "transgenic" animal, which is further described above.

Homologous recombination is commonly used to completely inactivate a gene (i.e., to produce a "knockout"). Constructs used for homologous recombination may be, for example, insertion constructs or replacement constructs. Insertion constructs contain a region of sequence homology to the target gene sequence and are introduced by homologous recombination into the homologous site of the target gene, thereby interrupting the target gene by adding sequences. In contrast, replacement constructs, which are more commonly used, contain two regions of homology to the target gene located on either side of the target gene sequence. Homologous recombination (by double crossover) then replaces the target gene sequences with the replacement-construct sequences (*Current Protocols in Molecular Biology*, John Wiley & Sons, Inc., "Manipulating the Mouse Genome", chapter 23.1, supplement 52–51 (2000)).

Gene inactivation by homologous recombination can be achieved in various ways. For example, a region of a gene involved in regulating expression may be interrupted (e.g., by introducing an insertion construct containing a positive selectable marker), thereby inhibiting or completely blocking production of normal mRNA and protein from the target gene. As an alternative to interrupting a gene by inserting a sequence, a gene may also be inactivated by deleting a portion of the gene or the entire gene. By using a construct having two separate regions of homology to the target gene (e.g., separated by up to about 15 kb), the sequences intervening the two homologous regions can be deleted. Alternatively, small mutations, such as a point mutation, can be introduced into the target gene sequence. Gene knockouts may also be controlled either spatially (e.g., in cell type- or tissue-specific knockouts) or temporally by modulating the activity or expression of recombinase in a CrelloxP recombinase system (*Current Protocols in Molecular Biology*, John Wiley & Sons, Inc., "Manipulating the Mouse Genome", chapter 23.1, supplement 52–51 (2000)).

Embryonic stem cell lines, from which knockout non-human animals may be produced, may be either heterozygous ("single knockout"; described in *Current Protocols in Molecular Biology*, John Wiley & Sons, Inc., "Manipulating the Mouse Genome", chapter 23.5, supplements 52–53 (2000–2001)) or homozygous ("double knockout"; described in *Current Protocols in Molecular Biology*, John Wiley & Sons, Inc., "Manipulating the Mouse Genome", chapter 23.6, supplements 52–53 (2000–2001)).

Methods for generating knockout non-human animals have become conventional in the art and are described in many patents and printed publications. For example, techniques for high-throughput generation of knockout mice (referred to as "gene trapping" technology), such as by using retrovirus integration, are described in U.S. Pat. Nos. 6,218,123; 6,207,371; 6,139,833; 6,136,566; and 6,080,576. Production of knockout mice by homologous recombination is described in *Current Protocols in Molecular Biology*, John Wiley & Sons, Inc., "Manipulating the Mouse Genome", chapter 23; Robertson, E. J. 1991. "Using embryonic stem cells to introduce mutations into the mouse germ line." *Biol. Reprod.* 44:238–245; and Zimmer, A. 1992. "Manipulating the genome by homologous recombination in embryonic stem cells." *Annu. Rev. Neurosci.* 15:115–137. Representative publications reviewing the production and use of knockout mice include, for example, "Knockout mice: a paradigm shift in modern immunology." Mak et al., *Nature Rev Immunol* 2001 October; 1(1): 1 1–9; "Mouse models for multistep tumorigenesis.", Wu et al., *Trends Cell Biol* 2001 November; 11(11):S2–9; "Mutant and genetically modified mice as models for studying the relationship between aging and carcinogenesis." Anisimov, *Mech Ageing Dev* 2001 September;122(12):1221–55; "Unraveling human cancer in the mouse: recent refinements to modeling and analysis.", Resor et al., *Hum Mol Genet* 2001 April; 10(7):669–75; "Gene-targeting strategies." Cheah et al., *Methods Mol Biol* 2000;136:455–63; "Mouse genetics/genomics: an effective approach for drug target discovery and validation." West et al., *Med Res Rev* 2000 May;20(3):216–30; "Understanding hypertension through genetic manipulation in mice.", Cvetkovic et al., *Kidney Int* 2000 Mar;57(3):863–74; and "Transgenic and gene knockout mice in cancer research.", Viney, *Cancer Metastasis Rev* 1995 June; 14(2):77–90.

EXAMPLES

Cloning of Monkey Cathepsin S cDNA

Poly-A mRNA was prepared from approximate $2\times10^7$ Cynomologous monkey peripheral blood mononuclear cells (PBMC) using oligo (dT)-cellulose according to the manufacturer's instructions (Invitrogen, San Diego, Calif.). The poly-A selected mRNA (0.05 μg) was used to synthesize and amplify a double-stranded cDNA pool using a SMART cDNA synthesis kit (Clontech, Palo Alto, Calif.). The Cynomologous cDNA encoding pro-CatS was PCR amplified from the cDNA pool using a BD Advantage 2 PCR kit (Clontech, Palo Alto, Calif.) using primers designed according to the monkey (*Saimiri boliviensis*) pro-CatS sequences [5' primer CCGGAATTCTTGCATAAAGATCCCAC-CCTGG (SEQ ID NO:8) and 3' primer ATAGTTTAGCG-GCCGCCTAGATTTCTGGGTAAGAGGGG (SEQ ID NO:9)]. The 1 Kb amplified DNA fragment was ligated to a pPIC 9 vector between EcoRI and Not I sites and the nucleotide sequence was determined. The 5'- and 3'-untranslated regions, including the pre-sequence of CatS and poly-A, were obtained by PCR amplification using a BD SMART RACE cDNA amplification kit using primers provided by the kit and two gene specific primers [GSP1: GGGATAGGAAGCGTCTGAGTCGATGCCG (SEQ ID NO:10) and GSP2: GGGCCCTGGAAGCACAGCT-GAAGC (SEQ ID NO:11)]. The DNA sequences determined from PCR products were used to assemble a full-length CatS cDNA (FIG. 1).

Expression of Cathepsin S

The pro-CatS sequence amplified from the cDNA pool was ligated to the restriction sites (EcoRI and Not I) in the multiple cloning site of a *Pichia* expression vector PIC9 to make a signal peptide fusion to the pro-CatS sequence. This expression construct forms a signal peptide-pro-CatS fusion under a methanol-inducible promoter and allows secretion of the pro-CatS protein to the culture medium upon removal of the signal peptide. The Pro-CatS expression plasmid was transformed into *Pichia,* and His+ transformants were selected. The expression of pro-CatS in methanol-induced culture medium was further confirmed by Western blot using human anti-CatS antibody.

Purification of Cathepsin S

Pro-cat S was produced by fermentation of yeast. Cell-free supernatant was filtered successively through 0.45 μm and 0.22 μm membranes. Filtered supernatant was further concentrated by ultrafiltration and diafiltrated to auto-activation buffer (50 mM NaOAc, 1 mM EDTA, and 1 mM DTT, pH 4.5). After sitting overnight at 4° C., the mature cat S was captured by SP fast flow and followed by separation on source 15S with salt gradient from 0 to 0.5 M. Fractions containing cat S activity were further confirmed by SDS-PAGE and Western blot.

Assay for Cathepsin S

An activity assay for cyno-Cat S was carried out using Z-VVR-AMC as substrate in a buffer containing 50 mM MES pH6.5, 100 mMNaCl, and 2.5 mM EDTA at room temperature. The reaction volume was 100 μl in a micro-titer reader plate and the RFU was collected over 5 minutes using an excitation filter of 360nm and an emission filter of 460 nm.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide, wherein the amino acid sequence of the polypeptide consists of SEQ ID NO:2.

2. An isolated polypeptide, wherein the amino acid sequence of the polypeptide comprises SEQ ID NO:2.

3. An isolated polypeptide, wherein the amino acid sequence of said polypeptide consists of an amino sequence having at least 99% sequence identity to SEQ ID NO:2.

4. An isolated polypeptide, wherein the amino acid sequence of said polypeptide comprises an amino acid sequence having at least 99% sequence identity to SEQ ID NO:2.

5. A fusion polypeptide, wherein the fusion polypeptide comprises the polypeptide of claim 2 fused to a heterologous amino add sequence.

6. A fusion polypeptide, wherein the fusion polypeptide comprises the polypeptide of claim 4 fused to a heterologous amino acid sequence.

7. A composition comprising the polypeptide of claim 1.
8. A composition comprising the polypeptide of claim 2.
9. A composition comprising the polypeptide of claim 3.
10. A composition comprising the polypeptide of claim 4.
11. A composition comprising the polypeptide of claim 5.
12. A composition comprising the polypeptide of claim 6.

* * * * *

SEQUENCE LISTING

```
<160> NUMBER OF SEQ ID NOS: 11

<210> SEQ ID NO 1
<211> LENGTH: 1798
<212> TYPE: DNA
<213> ORGANISM: Cynomologous monkey

<400> SEQUENCE: 1
agttgaactg aaatctccct gctgctgctt tgaaatctta gaagagagcc catcaattca      60
aggattctta ctgtaggagc acctgctggt tctatcacaa tgaaacagct ggtttgtgtg     120
ctcttggtgt gctcctctgc agtggcgcag ttgcataaag atcctaccct ggatcatcac     180
tggcatctct ggaagaaaac ctatggcaaa caatacaagg aaaagaatga agaagcagta     240
cgacgtctca tctgggaaaa gaatctaaag tttgtgatgc ttcataacct ggagcattca     300
atgggaatgc actcatatga tctgggcatg aaccacctgg gagacatgac cagtgaagaa     360
gtgatgtctt tgatgagttc cctgagagtt cccagccagt ggcagagaaa tatcacatat     420
aagtcaaacg ctaatcagat attgccggat tctgtggact ggagagagaa agggtgtgtt     480
actgaagtga aatatcaagg ttcttgtggt gcttgctggg ctttcagtgc tgtgggggcc     540
ctggaagcac agctgaagct gaaaacagga aagctggtgt ctctcagtgc ccagaacctg     600
gtggattgct caactgaaaa atatggaaac aaaggctgca atggtggctt catgacaagg     660
gctttccagt acatcattga taacaacggc atcgactcag acgcttccta tccctacaaa     720
gccacggatc agaagtgtca atatgactca aaatatcgtg ctgccacatg ttcaaagtat     780
actgaacttc cttatggcag agaagatgtc ctgaaagaag ttgtggccaa taaaggccca     840
gtgtctgttg gtgtggatgc gagtcatcct tctttcttcc tctacagaag tggtgtctac     900
tatgaaccat cctgtactca gaatgtgaat catggtgtac ttgtggttgg ctatggtgtt     960
cttaacggga aagaatactg gcttgtgaaa aacagctggg gccgcaactt tggtgaagaa    1020
ggatatattc ggatggcaag aaataaagga atcattgtg ggattgctag tttcccctct    1080
tacccagaaa tctagagagg atctcttctt tttataacaa atcaagaaaa tatgaagcac    1140
tttctcttaa cttaattttt cctgctgtat ccagaagaaa taattgtgtc acgattaatg    1200
tgtatttact gtactaatta aaaatatag tttgaggccg ggcacggtgg ctcacgcctg    1260
taatcccagt actttgggag gccaaggcag gcatatcaac ttgaggccag gagttaaaga    1320
caggcctggc taacatggtg aaaccccgtc tctactaaaa atacaaaaca ttagcggagc    1380
gtaatggtgc atgcctgtaa tcccagctac ttgggaggct gaagcacaag attccttgaa    1440
cccaagaggt tgaggctgtg gtgagctgag accacaccac tgtactccag cctggacaac    1500
agagtggaga ctctgtttca aaaaacaga aagataata tagtttgatt cttcgttttt    1560
taaaatttgc aaacctcagg aaaagtttg ctaagtaaat tagtagtgta ctatagatat    1620
aactgtataa aaattgttca acctaaaaca atctgtcatt gttcattgtt ttattttata    1680
```

```
ctctttgtct ttttaagacc cctgatagcc ttttgtaact tgatggctta aaagtactta    1740
ataaatctgc catttcaaat ttcatttcaa aaaaaaaaaa aaaaaaaaaa aaaaaaa       1798
```

<210> SEQ ID NO 2
<211> LENGTH: 331
<212> TYPE: PRT
<213> ORGANISM: Cynomologous monkey

<400> SEQUENCE: 2

```
Met Lys Gln Leu Val Cys Val Leu Leu Val Cys Ser Ser Ala Val Ala
 1               5                  10                  15

Gln Leu His Lys Asp Pro Thr Leu Asp His His Trp His Leu Trp Lys
                20                  25                  30

Lys Thr Tyr Gly Lys Gln Tyr Lys Glu Lys Asn Glu Glu Ala Val Arg
            35                  40                  45

Arg Leu Ile Trp Glu Lys Asn Leu Lys Phe Val Met Leu His Asn Leu
        50                  55                  60

Glu His Ser Met Gly Met His Ser Tyr Asp Leu Gly Met Asn His Leu
65                  70                  75                  80

Gly Asp Met Thr Ser Glu Glu Val Met Ser Leu Met Ser Ser Leu Arg
                85                  90                  95

Val Pro Ser Gln Trp Gln Arg Asn Ile Thr Tyr Lys Ser Asn Ala Asn
                100                 105                 110

Gln Ile Leu Pro Asp Ser Val Asp Trp Arg Glu Lys Gly Cys Val Thr
            115                 120                 125

Glu Val Lys Tyr Gln Gly Ser Cys Gly Ala Cys Trp Ala Phe Ser Ala
        130                 135                 140

Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Thr Glu Lys Tyr Gly
                165                 170                 175

Asn Lys Gly Cys Asn Gly Gly Phe Met Thr Arg Ala Phe Gln Tyr Ile
                180                 185                 190

Ile Asp Asn Asn Gly Ile Asp Ser Asp Ala Ser Tyr Pro Tyr Lys Ala
            195                 200                 205

Thr Asp Gln Lys Cys Gln Tyr Asp Ser Lys Tyr Arg Ala Ala Thr Cys
        210                 215                 220

Ser Lys Tyr Thr Glu Leu Pro Tyr Gly Arg Glu Asp Val Leu Lys Glu
225                 230                 235                 240

Val Val Ala Asn Lys Gly Pro Val Ser Val Gly Val Asp Ala Ser His
                245                 250                 255

Pro Ser Phe Phe Leu Tyr Arg Ser Gly Val Tyr Glu Pro Ser Cys
                260                 265                 270

Thr Gln Asn Val Asn His Gly Val Leu Val Val Gly Tyr Gly Val Leu
            275                 280                 285

Asn Gly Lys Glu Tyr Trp Leu Val Lys Asn Ser Trp Gly Arg Asn Phe
        290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330
```

<210> SEQ ID NO 3
<211> LENGTH: 330
<212> TYPE: PRT

<213> ORGANISM: Saimiri boliviensis

<400> SEQUENCE: 3

```
Met Lys Gln Leu Val Cys Val Leu Phe Val Cys Ser Ser Ala Val Thr
  1               5                  10                  15

Gln Leu His Lys Asp Pro Thr Leu Asp His His Trp Asn Leu Trp Lys
             20                  25                  30

Lys Thr Tyr Gly Lys Gln Tyr Lys Glu Lys Asn Glu Glu Ala Val Arg
         35                  40                  45

Arg Leu Ile Trp Glu Lys Asn Leu Lys Phe Val Met Leu His Asn Leu
 50                  55                  60

Glu His Ser Met Gly Met His Ser Tyr Asp Leu Gly Met Asn His Leu
 65                  70                  75                  80

Gly Asp Met Thr Ser Glu Glu Val Met Ser Leu Met Ser Ser Leu Arg
                 85                  90                  95

Val Pro Asn Gln Trp Gln Arg Asn Ile Thr Tyr Lys Ser Asn Pro Asn
             100                 105                 110

Gln Met Leu Pro Asp Ser Val Asp Trp Arg Glu Lys Gly Cys Val Thr
         115                 120                 125

Glu Val Lys Tyr Gln Gly Ser Cys Gly Ala Cys Trp Ala Phe Ser Ala
     130                 135                 140

Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Glu Lys Tyr Gly Asn
                 165                 170                 175

Lys Gly Cys Asn Gly Gly Phe Met Thr Glu Ala Phe Gln Tyr Ile Ile
             180                 185                 190

Asp Asn Lys Gly Ile Asp Ser Glu Ala Ser Tyr Pro Tyr Lys Ala Thr
         195                 200                 205

Asp Gln Lys Cys Gln Tyr Asp Ser Lys Tyr Arg Ala Ala Thr Cys Ser
     210                 215                 220

Lys Tyr Thr Glu Leu Pro Tyr Gly Arg Glu Asp Val Leu Lys Glu Ala
225                 230                 235                 240

Val Ala Asn Lys Gly Pro Val Cys Val Gly Val Asp Ala Ser His Pro
                 245                 250                 255

Ser Phe Phe Leu Tyr Arg Ser Gly Val Tyr Tyr Asp Pro Ala Cys Thr
             260                 265                 270

Gln Lys Val Asn His Gly Val Leu Val Ile Gly Tyr Gly Asp Leu Asn
         275                 280                 285

Gly Lys Glu Tyr Trp Leu Val Lys Asn Ser Trp Gly Ser Asn Phe Gly
     290                 295                 300

Glu Gln Gly Tyr Ile Arg Met Ala Arg Asn Lys Gly Asn His Cys Gly
305                 310                 315                 320

Ile Ala Ser Tyr Pro Ser Tyr Pro Glu Ile
                 325                 330
```

<210> SEQ ID NO 4
<211> LENGTH: 331
<212> TYPE: PRT
<213> ORGANISM: Homo sapiens

<400> SEQUENCE: 4

```
Met Lys Arg Leu Val Cys Val Leu Leu Val Cys Ser Ser Ala Val Ala
  1               5                  10                  15

Gln Leu His Lys Asp Pro Thr Leu Asp His His Trp His Leu Trp Lys
```

-continued

```
                    20                  25                  30
Lys Thr Tyr Gly Lys Gln Tyr Lys Glu Lys Asn Glu Glu Ala Val Arg
                35                  40                  45

Arg Leu Ile Trp Glu Lys Asn Leu Lys Phe Val Met Leu His Asn Leu
         50                  55                  60

Glu His Ser Met Gly Met His Ser Tyr Asp Leu Gly Met Asn His Leu
 65                  70                  75                  80

Gly Asp Met Thr Ser Glu Glu Val Met Ser Leu Met Ser Ser Leu Arg
                 85                  90                  95

Val Pro Ser Gln Trp Gln Arg Asn Ile Thr Tyr Lys Ser Asn Pro Asn
                100                 105                 110

Trp Ile Leu Pro Asp Ser Val Asp Trp Arg Glu Lys Gly Cys Val Thr
            115                 120                 125

Glu Val Lys Tyr Gln Gly Ser Cys Gly Ala Cys Trp Ala Phe Ser Ala
        130                 135                 140

Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
            180                 185                 190

Ile Asp Asn Lys Gly Ile Asp Ser Asp Ala Ser Tyr Pro Tyr Lys Ala
        195                 200                 205

Met Asp Gln Lys Cys Gln Tyr Asp Ser Lys Tyr Arg Ala Ala Thr Cys
    210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
            260                 265                 270

Thr Gln Asn Val Asn His Gly Val Leu Val Val Gly Tyr Gly Asp Leu
        275                 280                 285

Asn Gly Lys Glu Tyr Trp Leu Val Lys Asn Ser Trp Gly His Asn Phe
    290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330
```

<210> SEQ ID NO 5
<211> LENGTH: 331
<212> TYPE: PRT
<213> ORGANISM: Canis familiaris

<400> SEQUENCE: 5

```
Met Lys Trp Leu Val Gly Leu Leu Pro Leu Cys Ser Tyr Ala Val Ala
  1               5                  10                  15

Gln Val His Lys Asp Pro Thr Leu Asp His His Trp Asn Leu Trp Lys
                 20                  25                  30

Lys Thr Tyr Ser Lys Gln Tyr Lys Glu Glu Asn Glu Glu Val Ala Arg
                35                  40                  45

Arg Leu Ile Trp Glu Lys Asn Leu Lys Phe Val Met Leu His Asn Leu
         50                  55                  60
```

```
Glu His Ser Met Gly Met His Ser Tyr Asp Leu Gly Met Asn His Leu
 65                  70                  75                  80

Gly Asp Met Thr Gly Glu Val Ile Ser Leu Met Gly Ser Leu Arg
                 85                  90                  95

Val Pro Ser Gln Trp Gln Arg Asn Val Thr Tyr Arg Ser Asn Ser Asn
                100                 105                 110

Gln Lys Leu Pro Asp Ser Val Asp Trp Arg Glu Lys Gly Cys Val Thr
            115                 120                 125

Glu Val Lys Tyr Gln Gly Ser Cys Gly Ala Cys Trp Ala Phe Ser Ala
            130                 135                 140

Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
            180                 185                 190

Ile Asp Asn Asn Gly Ile Asp Ser Glu Ala Ser Tyr Pro Tyr Lys Ala
            195                 200                 205

Met Asn Gly Lys Cys Arg Tyr Asp Ser Lys Lys Arg Ala Ala Thr Cys
    210                 215                 220

Ser Lys Tyr Thr Glu Leu Pro Phe Gly Ser Glu Asp Ala Leu Lys Glu
225                 230                 235                 240

Ala Val Ala Asn Lys Gly Pro Val Ser Val Ala Ile Asp Ala Ser His
                245                 250                 255

Tyr Ser Phe Phe Leu Tyr Arg Ser Gly Val Tyr Tyr Glu Pro Ser Cys
            260                 265                 270

Thr Gln Asn Val Asn His Gly Val Leu Val Val Gly Tyr Gly Asn Leu
            275                 280                 285

Asn Gly Lys Asp Tyr Trp Leu Val Lys Asn Ser Trp Gly Leu Asn Phe
    290                 295                 300

Gly Asp Gln Gly Tyr Ile Arg Met Ala Arg Asn Ser Gly Asn His Cys
305                 310                 315                 320

Gly Ile Ala Ser Tyr Pro Ser Tyr Pro Glu Ile
                325                 330

<210> SEQ ID NO 6
<211> LENGTH: 330
<212> TYPE: PRT
<213> ORGANISM: Mus musculus

<400> SEQUENCE: 6

Met Ala Val Leu Asp Ala Pro Gly Val Leu Cys Gly Asn Gly Ala Thr
 1               5                  10                  15

Ala Glu Arg Pro Thr Leu Asp His His Trp Asp Leu Trp Lys Lys Thr
                 20                  25                  30

His Glu Lys Glu Tyr Lys Asp Lys Asn Glu Glu Val Arg Arg Leu
             35                  40                  45

Ile Trp Glu Lys Asn Leu Lys Phe Ile Met Ile His Asn Leu Glu Tyr
         50                  55                  60

Ser Met Gly Met His Thr Tyr Gln Val Gly Met Asn Asp Met Gly Asp
 65                  70                  75                  80

Met Thr Asn Glu Glu Ile Leu Cys Arg Met Gly Ala Leu Arg Ile Pro
                 85                  90                  95

Arg Gln Ser Pro Lys Thr Val Thr Phe Arg Ser Tyr Ser Asn Arg Thr
                100                 105                 110
```

```
Leu Pro Asp Thr Val Asp Trp Arg Glu Lys Gly Cys Val Thr Glu Val
            115                 120                 125

Lys Tyr Gln Gly Ser Cys Gly Ala Cys Trp Ala Phe Ser Ala Val Gly
    130                 135                 140

Ala Leu Glu Gly Gln Leu Lys Leu Lys Thr Gly Lys Leu Ile Ser Leu
145                 150                 155                 160

Ser Ala Gln Asn Leu Val Asp Cys Ser Asn Glu Glu Lys Tyr Gly Asn
                165                 170                 175

Lys Gly Cys Gly Gly Gly Tyr Met Thr Glu Ala Phe Gln Tyr Ile Ile
            180                 185                 190

Asp Asn Gly Gly Ile Glu Ala Asp Ala Ser Tyr Pro Tyr Lys Ala Met
            195                 200                 205

Asp Glu Lys Cys His Tyr Asn Ser Lys Asn Arg Ala Ala Thr Cys Ser
        210                 215                 220

Arg Tyr Ile Gln Leu Pro Phe Gly Asp Glu Asp Ala Leu Lys Glu Ala
225                 230                 235                 240

Val Ala Thr Lys Gly Pro Val Ser Val Gly Ile Asp Ala Ser His Ser
                245                 250                 255

Ser Phe Phe Phe Tyr Lys Ser Gly Val Tyr Asp Asp Pro Ser Cys Thr
                260                 265                 270

Gly Asn Val Asn His Gly Val Leu Val Val Gly Tyr Gly Thr Leu Asp
            275                 280                 285

Gly Lys Asp Tyr Trp Leu Val Lys Asn Ser Trp Gly Leu Asn Phe Gly
        290                 295                 300

Asp Gln Gly Tyr Ile Arg Met Ala Arg Asn Asn Lys Asn His Cys Gly
305                 310                 315                 320

Ile Ala Ser Tyr Cys Ser Tyr Pro Glu Ile
                325                 330

<210> SEQ ID NO 7
<211> LENGTH: 322
<212> TYPE: PRT
<213> ORGANISM: Unknown
<220> FEATURE:
<223> OTHER INFORMATION: consensus sequence

<400> SEQUENCE: 7

Met Lys Leu Val Cys Val Leu Val Cys Ser Ser Ala Val Ala Gln Leu
1               5                   10                  15

His Lys Asp Pro Thr Leu Asp His His Trp Leu Trp Lys Lys Thr Tyr
                20                  25                  30

Gly Lys Gln Tyr Lys Glu Lys Asn Glu Glu Ala Val Arg Arg Leu Ile
            35                  40                  45

Trp Glu Lys Asn Leu Lys Phe Val Met Leu His Asn Leu Glu His Ser
    50                  55                  60

Met Gly Met His Ser Tyr Asp Leu Gly Met Asn His Leu Gly Asp Met
65                  70                  75                  80

Thr Ser Glu Glu Val Met Ser Leu Met Ser Ser Leu Arg Val Pro Ser
                85                  90                  95

Gln Trp Gln Arg Asn Ile Thr Tyr Lys Ser Asn Asn Gln Leu Pro Asp
            100                 105                 110

Ser Val Asp Trp Arg Glu Lys Gly Cys Val Thr Glu Val Lys Tyr Gln
        115                 120                 125

Gly Ser Cys Gly Ala Cys Trp Ala Phe Ser Ala Val Gly Ala Leu Glu
    130                 135                 140
```

```
Ala Gln Leu Lys Leu Lys Thr Gly Lys Leu Val Ser Leu Ser Ala Gln
145                 150                 155                 160

Asn Leu Val Asp Cys Ser Thr Glu Lys Tyr Gly Asn Lys Gly Cys Asn
            165                 170                 175

Gly Gly Phe Met Thr Ala Phe Gln Tyr Ile Ile Asp Asn Gly Ile Asp
            180                 185                 190

Ser Asp Ala Ser Tyr Pro Tyr Lys Ala Met Asp Gln Lys Cys Gln Tyr
            195                 200                 205

Asp Ser Lys Tyr Arg Ala Ala Thr Cys Ser Lys Tyr Thr Glu Leu Pro
    210                 215                 220

Tyr Gly Arg Glu Asp Val Leu Lys Glu Ala Val Ala Asn Lys Gly Pro
225                 230                 235                 240

Val Ser Val Gly Val Asp Ala Ser His Pro Ser Phe Phe Leu Tyr Arg
            245                 250                 255

Ser Gly Val Tyr Tyr Glu Pro Ser Cys Thr Gln Asn Val Asn His Gly
            260                 265                 270

Val Leu Val Val Gly Tyr Gly Leu Asn Gly Lys Glu Tyr Trp Leu Val
            275                 280                 285

Lys Asn Ser Trp Gly Asn Phe Gly Glu Gln Gly Tyr Ile Arg Met Ala
    290                 295                 300

Arg Asn Lys Gly Asn His Cys Gly Ile Ala Ser Tyr Pro Ser Tyr Pro
305                 310                 315                 320

Glu Ile

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
ccggaattct tgcataaaga tcccaccctg g                              31

<210> SEQ ID NO 9
<211> LENGTH: 38
<212> TYPE: DNA
<213> ORGANISM: Artificial Sequence
<220> FEATURE:
<223> OTHER INFORMATION: primer

<400> SEQUENCE: 9
atagtttagc ggccgcctag atttctgggt aagagggg                       38

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
gggataggaa gcgtctgagt cgatgccg                                  28

<210> SEQ ID NO 11
<211> LENGTH: 24
<212> TYPE: DNA
<213> ORGANISM: Artificial Sequence
<220> FEATURE:
<223> OTHER INFORMATION: primer
```

```
<400> SEQUENCE: 11
gggccctgga agcacagctg aagc                                              24
```